(12) United States Patent
Kolb et al.

(10) Patent No.: US 7,891,358 B2
(45) Date of Patent: Feb. 22, 2011

(54) CONTROLLABLE VALVE AND INHALATION DEVICE

(75) Inventors: Tobias Kolb, Munich (DE); Sascha Roeder, Munich (DE)

(73) Assignee: Activaero GmbH (DE)

( * ) Notice: Subject to any disclaimer, the term of this patent is extended or adjusted under 35 U.S.C. 154(b) by 851 days.

(21) Appl. No.: 11/427,567

(22) Filed: Jun. 29, 2006

(65) Prior Publication Data

US 2007/0006883 A1 Jan. 11, 2007

(30) Foreign Application Priority Data

Jul. 6, 2005 (EP) .................... 05014700

(51) Int. Cl.
*A61M 11/00* (2006.01)
(52) U.S. Cl. ................. 128/205.24
(58) Field of Classification Search ........... 128/205.24; 137/175; 138/45, 46
See application file for complete search history.

(56) References Cited

U.S. PATENT DOCUMENTS

| | | | |
|---|---|---|---|
| 4,756,508 A * | 7/1988 | Giachino et al. ............ 251/331 |
| 5,584,288 A * | 12/1996 | Baldwin ................. 128/202.28 |
| 5,655,520 A | 8/1997 | Howe et al. |
| 5,842,467 A | 12/1998 | Greco |
| 5,884,667 A * | 3/1999 | North .......................... 138/43 |
| 6,681,762 B1 | 1/2004 | Scheuch et al. |
| 7,131,440 B2 * | 11/2006 | Sonntag ................. 128/203.12 |
| 7,364,571 B2 * | 4/2008 | Schinazi et al. ............. 604/246 |
| 2001/0035187 A1 * | 11/2001 | Smith et al. ............ 128/205.24 |

FOREIGN PATENT DOCUMENTS

| | | |
|---|---|---|
| DE | 19912461 A | 9/2000 |
| EP | 0050654 B | 5/1982 |
| EP | 0965355 A | 12/1999 |
| EP | 1036569 A | 9/2000 |
| EP | 1038544 A | 9/2000 |
| EP | 1136921 A | 9/2001 |

* cited by examiner

*Primary Examiner*—Steven O Douglas
(74) *Attorney, Agent, or Firm*—Faegre & Benson LLP

(57) ABSTRACT

The present invention relates to an improved controllable valve, in particular for an inhalation device, which, e.g., comprises a container for a predetermined aerosol volume, a means for disbursing an aerosol from an aerosol dispenser into the container and a control means that keeps the inhalation flow essentially constant during the entire inhalation. The control means comprises an either continuously or gradually controllable valve so as to limit the flow rate.

29 Claims, 11 Drawing Sheets

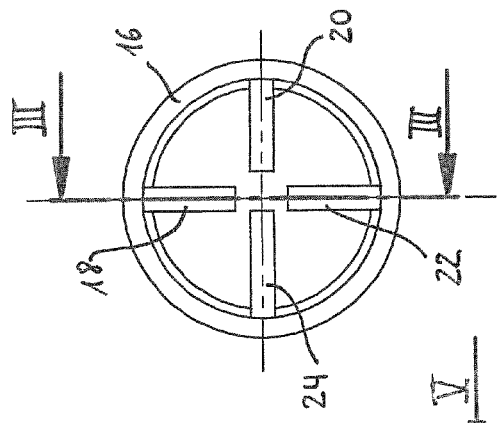
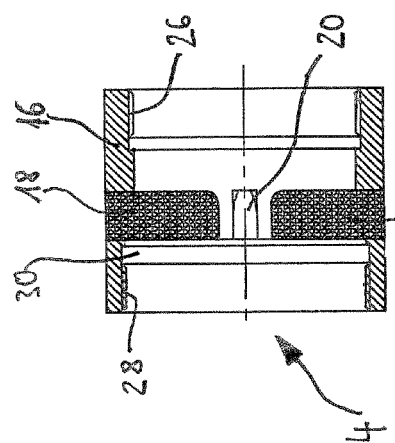
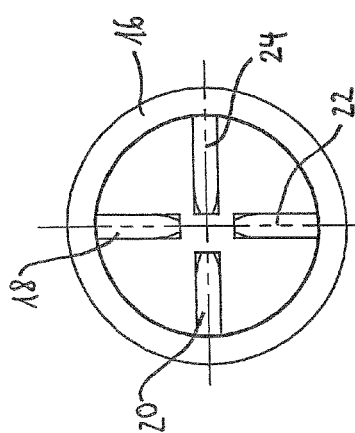
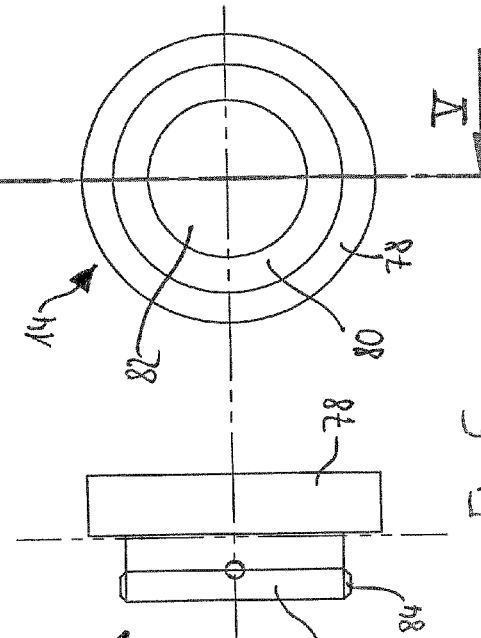
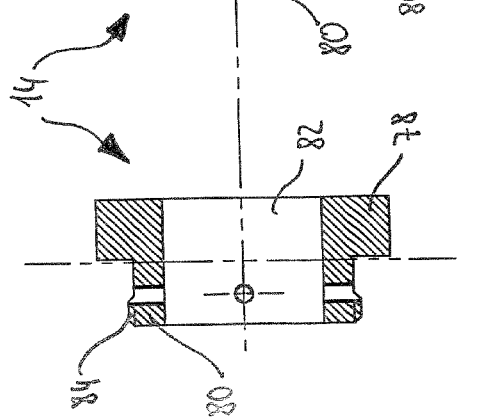

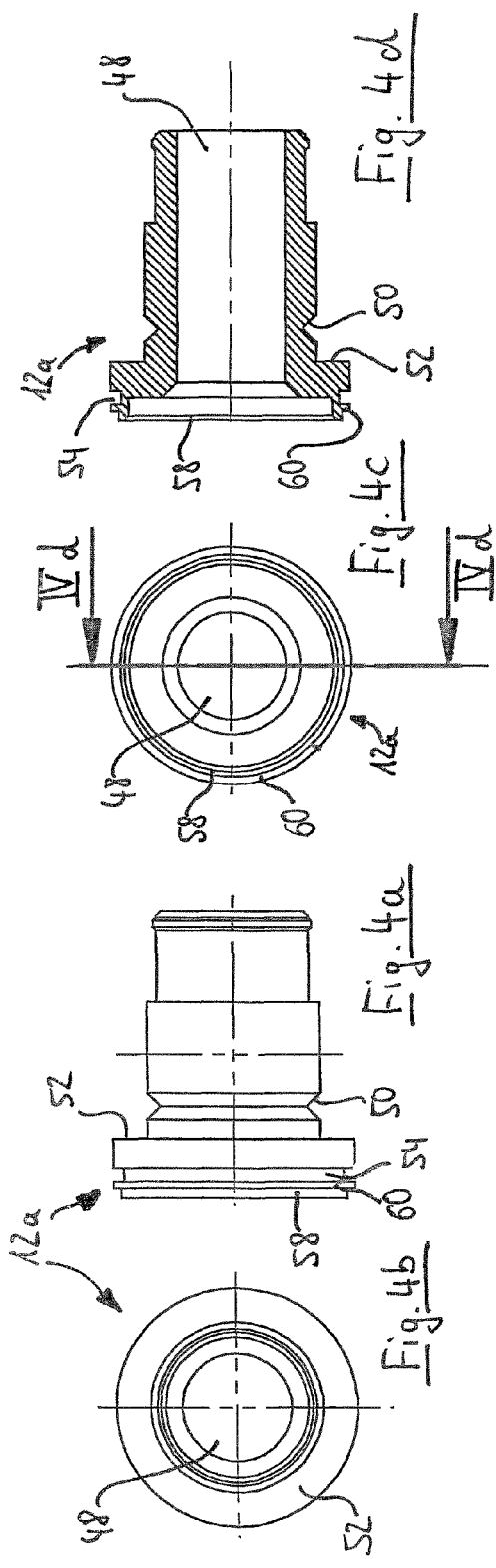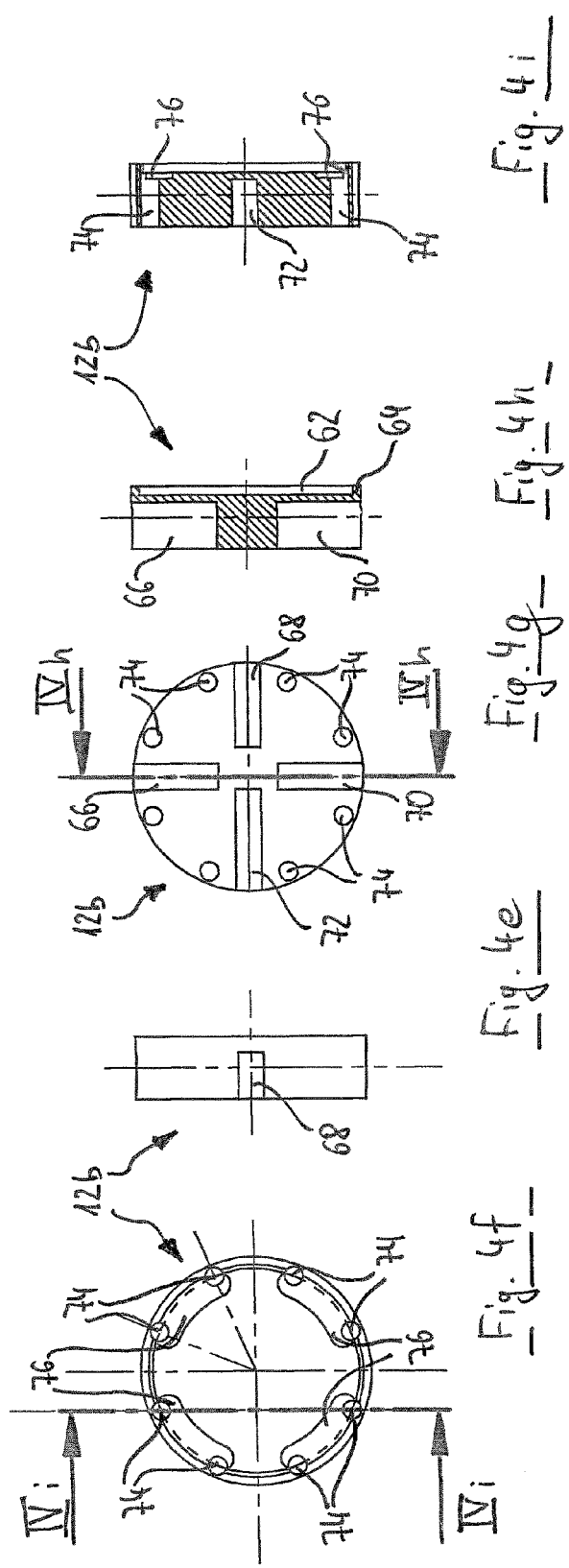

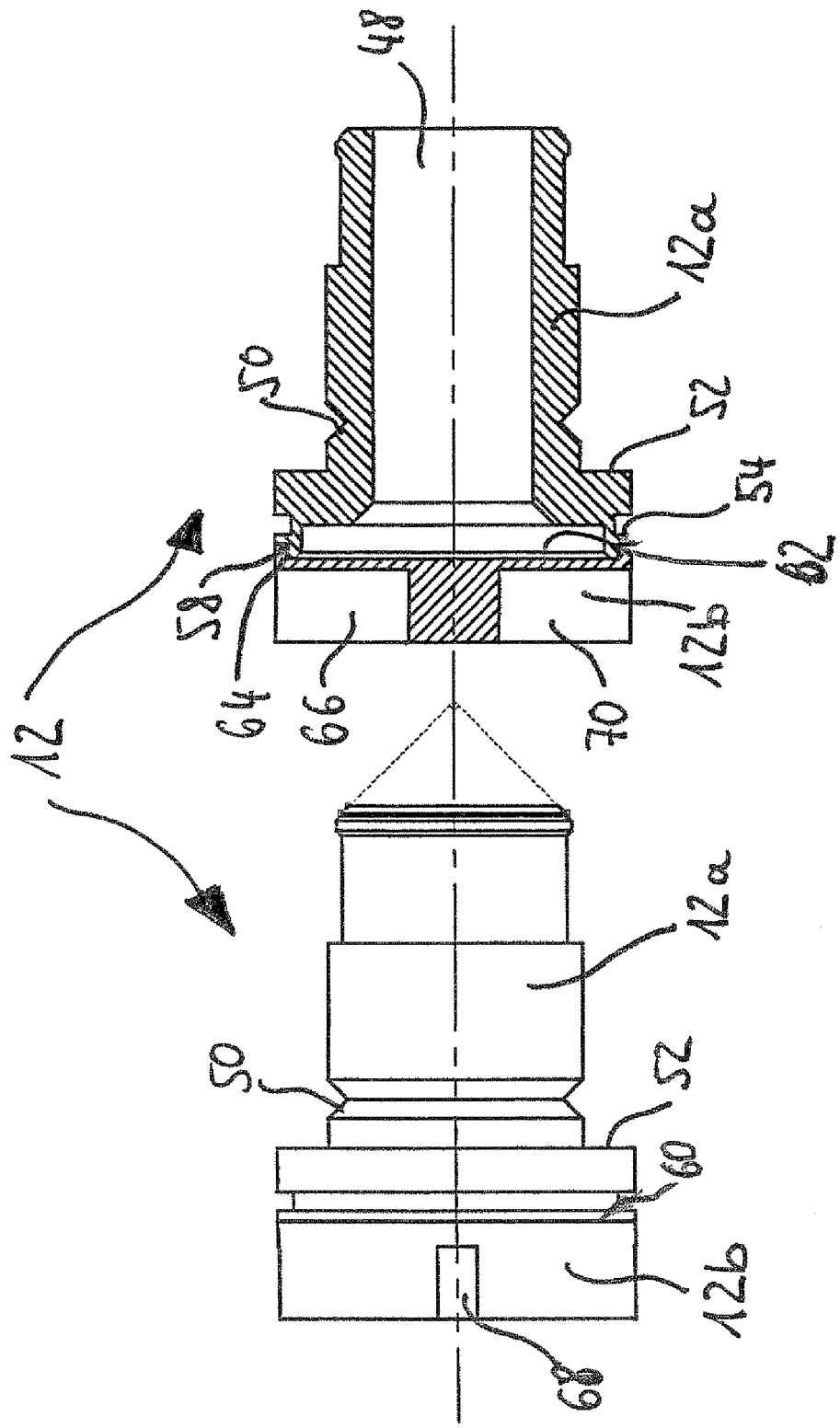

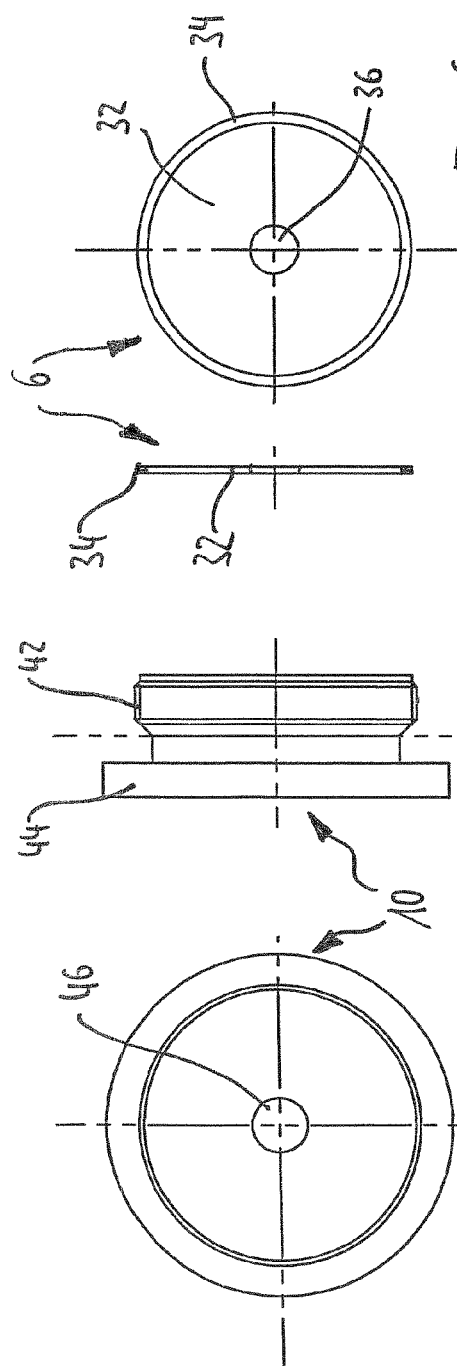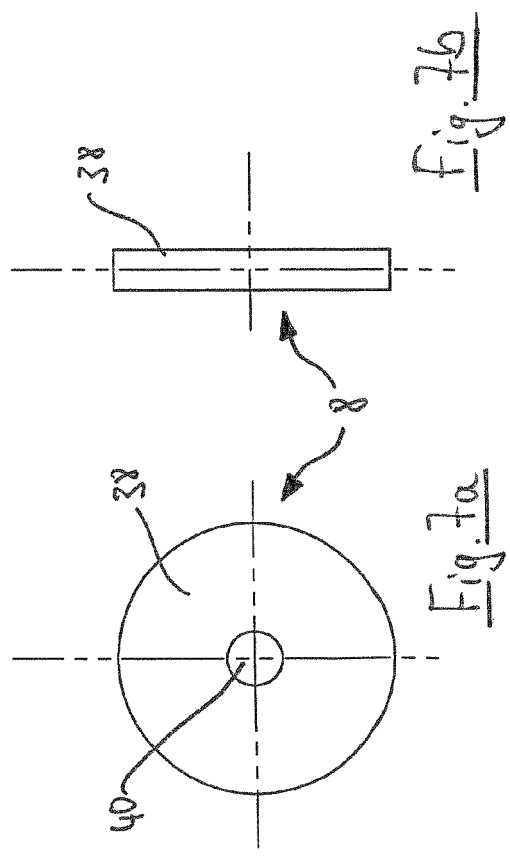

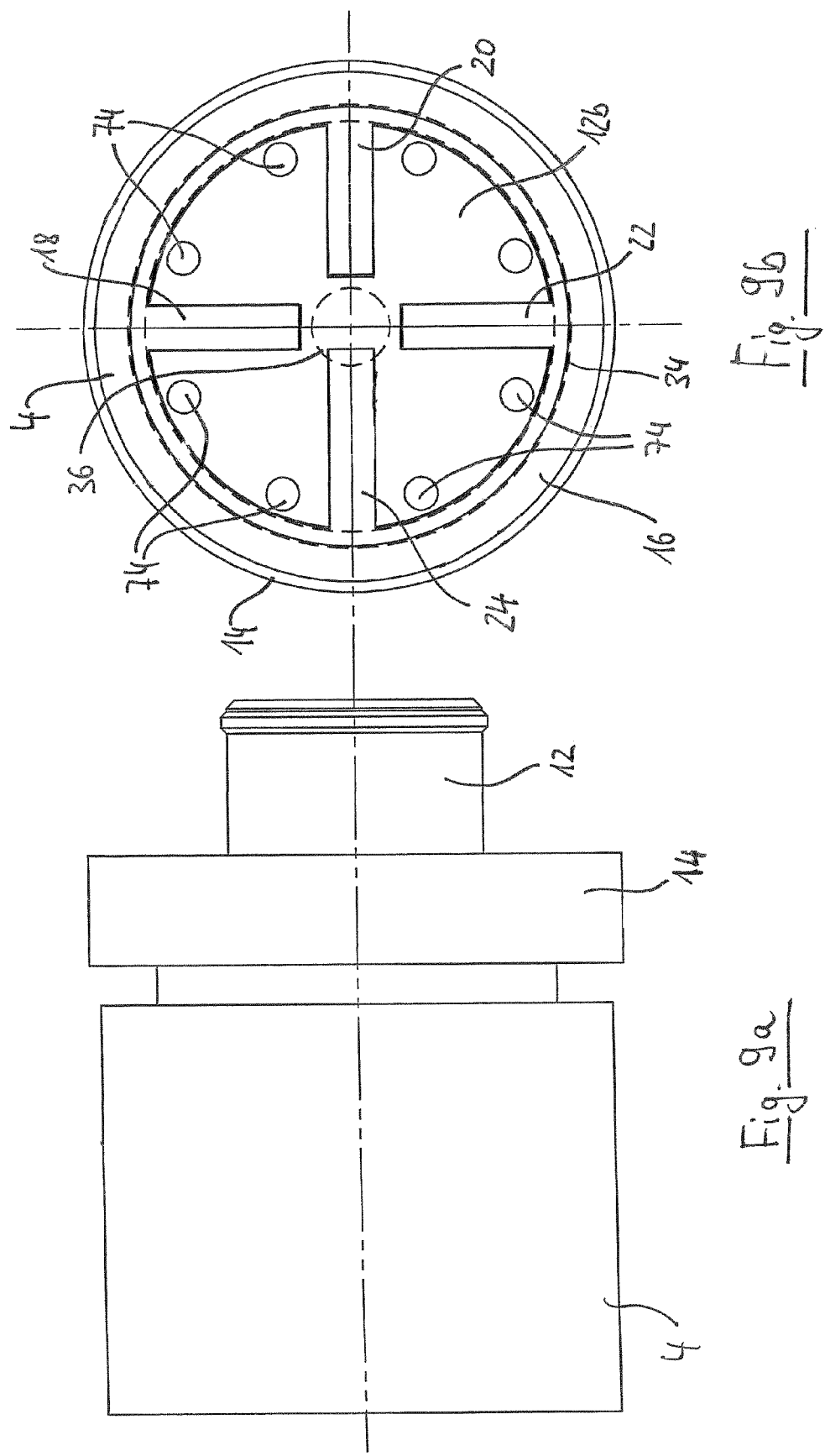

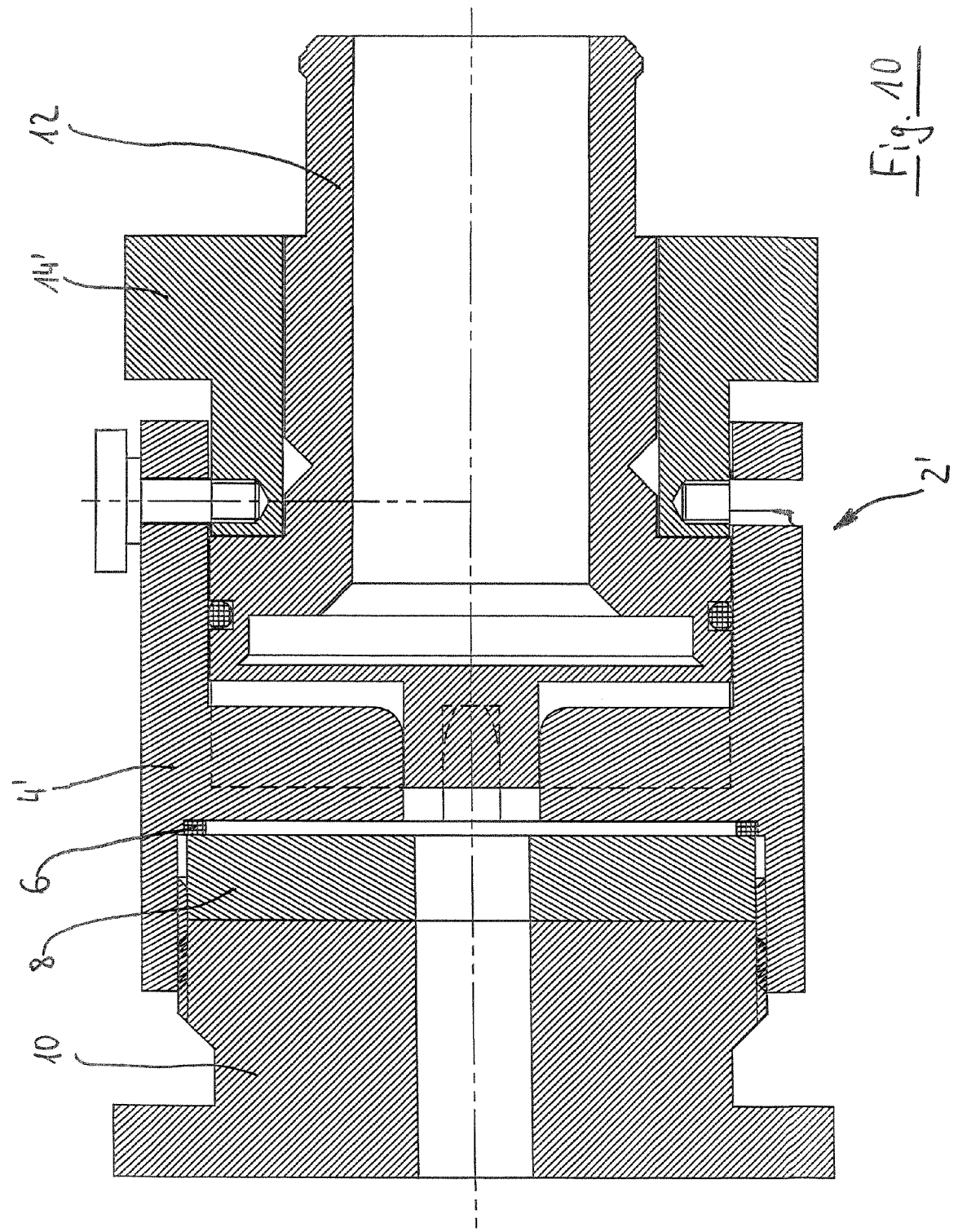

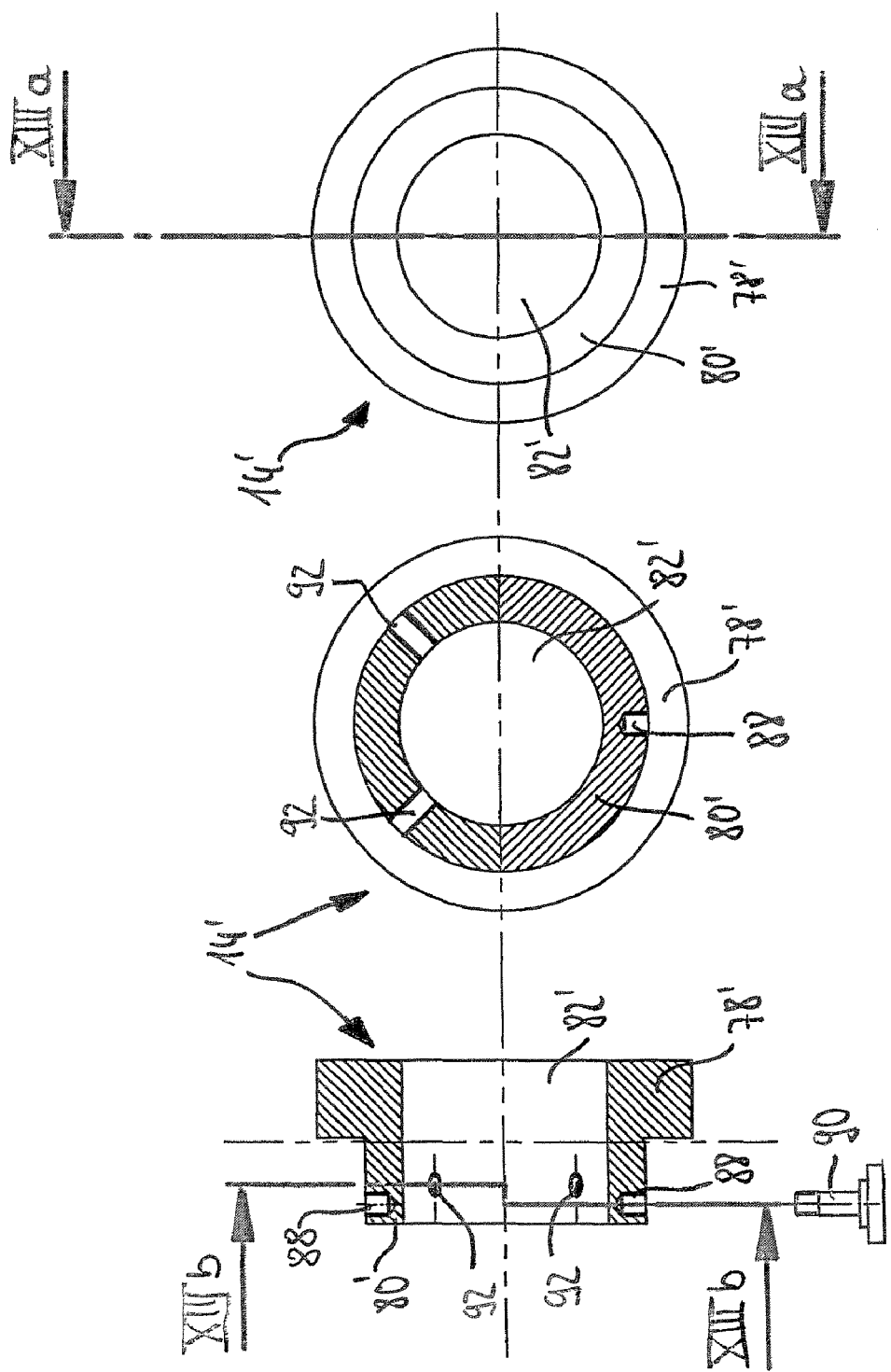

CONTROLLABLE VALVE AND INHALATION DEVICE

REFERENCE TO RELATED APPLICATION

This application claims priority to European Patent Application 05 01 4700.8 filed Jul. 6, 2005.

The present invention relates to a controllable valve and a device for the inhalation of drug doses in the form of aerosols into the lungs. Suitable drugs are analgesics, angina remedies, anti-allergic agents, antihistamines and anti-inflammatory drugs, expectorants, antitussives, bronchodilators, diuretics, anticholinergics, corticoids, xantines, anti-cancer drugs, therapeutically active proteins or peptides such as insulin or interferon, antioxidants, anti-inflammatory substances, active ingredients or drugs as well as combinations thereof.

The administration of drugs for the treatment of respiratory diseases, such as asthma, as well as prophylactics and drugs for the treatment of the mucosae of the tracheobronchial tract is preferred. The administration of corticoids is possible.

A further preferred field of application consists in a variable limitation of the respiratory flow rate in diagnostic apparatuses for pulmonary diseases. This is possible in all measuring methods using, e.g., aerosol particles for the diagnosis.

BACKGROUND

DE-A-199 12 461 discloses a device for flow rate limitation at low differential pressures, particularly for limiting the volumetric inhalation flow during inhalation of therapeutic aerosols. The device consists of a housing including an aspiration orifice, an inhalation orifice and a flow passage disposed therebetween. The flow passage has a flat elongate cross-section with flexible large-area walls. The cross-section of the flow passage is adapted to be reduced as a function of the differential pressure prevailing between the inhalation orifice and the aspiration orifice as well as of the flexibility of the material of the walls to a size appropriate for a predetermined volumetric maximum inhalation flow.

The administration of drugs in aerosol form by inhalation into the lungs is influenced essentially by four factors: (i) the particle size and the particle properties of the aerosol; (ii) the patient's tidal volume; (iii) the patient's respiratory flow; and (iv) the patient's morphometry and respiratory system. So far, the known systems have produced aerosols with suitable particle size ranges, however, they have only insufficiently or not at all considered the parameters "tidal volume" and "respiratory flow" (respiratory velocity). The aerosol inhalation is therefore uncontrolled so that the amount of aerosol particles provided to the lungs is insufficient or the lung areas to be treated (such as the alveolic area) are not at all provided with aerosol particles.

EP-A-0 965 355 discloses a device for a controlled inhalational administration of controlled dosage drugs into the lungs. This controlled inhalator comprises a closed recipient that is adapted to be charged with a predeterminable aerosol volume and from which the aerosol can be extracted via of a control means for the inhalation flow rate. In this known inhalator, the control means is either a controllable valve or a critical nozzle. The tidal flow can be limited by the use of a controllable valve or a critical nozzle.

EP-B-0 050 654 discloses an inhalation apparatus for administering pulmonary medication. This apparatus comprises an inflatable envelope from which an aerosol may be inhaled by means of a mouthpiece. Before inhalation, this aerosol is introduced into the inflatable envelope from a cartridge via a nebulizer. For limitation of the air flow rate through the mouthpiece during the inhalation, the mouthpiece is provided with a restriction. This restriction limits the tidal flow during the inhalation.

The two aforementioned inhalation devices are characterised in that the flow rate is limited so that during the inspiration phase the tidal volume is increased merely slowly and the increase in the tidal flow is decreased continuously. Thus, in a diagram showing the tidal flow over time, the graph is continuously flattened. On account of this flow limitation, the tidal flow increases in different manners to a maximum flow value as a function of the patient's sucking capacity. This results in an almost constant flow rate so that in the known inhalators the flow rate limitation may lead to a more constant aerosol deposition in the lungs.

EP-A-1 036 569 discloses a method and a device for providing a predetermined constant medicament dose for an inhalational administration at a low inhalation flow rate. This device comprises a closed container whose volume is reducible, a mouthpiece which is connected to the container and may be joined with a powder aerosol inhalator for providing a powder aerosol, a closed inner housing which surrounds the container, whose volume is reducible and from which the mouthpiece extends in a sealed manner and means for controlling the air flowing into or out of the area between the container and the housing. The housing may be brought from a state of reduced volume to a predetermined expanded state for filling the container with the predetermined aerosol volume.

Moreover, EP-A-1 038 544 discloses a device for flow rate limitation at low differential pressures, particularly for limiting the volumetric inhalation flow during inhalation of therapeutic aerosols. This device consists of a housing with at least one aspiration orifice, at least one inhalation orifice and a flow space disposed therebetween and including at least one flexible wall having a cross-section which can be reduced as a function of the differential pressure prevailing between said inhalation orifice and said aspiration orifice and of the flexibility of the wall material up to a predetermined dimension for a definable maximum volumetric inhalation flow.

Moreover, U.S. Pat. No. 5,655,520 discloses a flexible valve for administering constant flow rates of medicine.

U.S. Pat. No. 5,842,467 discloses a metered dose inhaler.

EP-A-1 136 921 discloses an inhalation device comprising a self-expandable container for a predetermined aerosol volume, means for disbursing an aerosol from an aerosol dispenser into the container and control means for controlling the inhalation flow. The control means keeps the inhalation flow essentially constant during the entire aerosol inhalation and comprises four flow channels radially extending between a central admission opening and discharge openings that are radially spaced apart from the admission opening. The four radially extending flow channels are formed by four radially arranged rectangular webs extending from an essentially rigid wall to an essentially flexible wall. One web thereof is longer than the others.

The present invention is based on the object of providing an improved control means and an improved valve that is in particular applicable in an inhalation device and supplies the tidal volume necessary for the aerosol inhalation irrespective of the patient's characteristics while being suitable for variable applications. This object is achieved by a valve or an inhalation device having the features of the claims.

The inhalation device of the present invention keeps the inhalation flow essentially constant during the entire aerosol inhalation and comprises a controllable valve for limiting the flow rate through the control means. The valve is preferably a variable flow limiter which, for example, allows for a continuous or gradual flow control.

The controllable valve according to the invention preferably comprises a housing, a set piston, a flexible wall (such as a membrane or an elastomer disk), an optional pressure plate, a closure element and an adjusting screw. The housing is preferably essentially tubular and comprises a plurality of, e.g. four, radially arranged webs, one of which is longer than the others. These webs extend from the tubular wall of the housing radially inwards in an axial view, the webs are arranged in a central portion of the housing so that on one side of the webs the housing is adapted to adjustably receive the set piston and on the opposite side of the webs it is adapted to receive the membrane or elastomer disk, the pressure plate and the closure element.

Moreover, the inhalation device according to the present invention is preferably designed such that the elastomer disk is forced against the webs of the housing by means of the pressure plate and the closure element so that a space is formed between the membrane and the set piston. To this end, the set piston comprises a plurality of, e.g. four, recesses that are radially arranged at the housing in correspondence with the webs, preferably at an end face facing the elastomer disk, one recess being longer than the others. A plurality of, e.g. two, admission openings are provided between two adjoining webs. These admission openings are for example on a common circumferential line and are spaced apart from each other by 45°. In an inner area of the set piston facing away from the recesses, the admission openings run into a common central flow channel. To this end, the set piston preferably consists of two parts. The first part comprises the recesses with the admission openings and the second part, which is preferably permanently connected, e.g. glued, to the first part, comprises the central flow channel to which the admission openings are connected.

The set piston is preferably sealingly received by the housing. Moreover, the adjusting screw may preferably be axially fixed to the set piston so that the set piston is axially adjustable with respect to the housing via the adjusting screw. To this end, the adjusting screw is preferably provided with an external thread that is engageable with a corresponding internal thread provided in the housing. By adjusting the adjusting screw, the piston may thus be axially shifted so that the webs provided at the housing may be inserted into the recesses provided at the set piston at will.

According to a further embodiment, the controllable valve according to the present invention is gradually adjustable. To this end, a sliding block guide is provided between the set piston and the housing. Moreover, the components of the controllable valve are essentially identical to those of the first embodiment.

Preferably, the controllable valve is connected to an inhalation limiter. The inhalation flow rate limitation for example consists of an inhalation bag, a bucket wheel or a ventilation channel that is closed after a predetermined period of time. The administered volume may be inferred from the predetermined flow rate and the measured inhalation time. As soon as this is achieved, the admission opening is closed. This means that the flow rate is indirectly measured by measuring the inhalation time. Both a mechanical as well as an electronic measurement of the volume is conceivable.

An inhalation device comprising the controllable valve according to the present invention keeps the inhalation flow rate essentially constant during the entire aerosol inhalation. Thus, the inhalation flow rate is increased to a maximum value directly at the beginning of the inspiration phase, which is necessary for a sufficient aerosol administration, and is held at this maximum value as long as a minimum pressure is generated by the patient during the inhalation. Preferably, this minimum pressure is not exceeding 10 mbar and is preferably in a range between 5 and 10 mbar. Thus, a flow rate limitation is already achieved at low differential pressures.

The inhalation device preferably combines a container, particularly self-expanding container, for a predetermined aerosol volume, means for disbursing an aerosol from an aerosol dispenser into the container and control means for controlling the inhalation flow rate, wherein the control means comprises a controllable valve according to the invention so as to keep the inhalation flow rate essentially constant during the entire inhalation.

The flow channel preferably runs into the inside of the housing which surrounds the aerosol container. Before the aerosol inhalation, the aerosol is led into the inside of the container from, e.g., a cartridge, preferably via a nozzle, such as a nebulizer or a controlled aerosol dosing supply. The container expands until in its fully expanded state an aerosol volume that is determined by the container volume is generated inside the container. Alternatively, it is also possible to arrange the aerosol volume directly at the nebulizer or at the aerosol dosing supply.

When the patient sucks the aerosol out of the container via a preferably provided mouthpiece, the container shrinks on account of the suction. The low pressure generated inside the housing is compensated via the flow channel. The generated low pressure arches the flexible wall towards the inside of the flow channel as a function of the extent of the low pressure so that the cross-section of the flow channel is reduced. This reduction in cross-section results in a limitation of the air flow through the flow channel into the housing inside for pressure compensation reasons, which in turn limits the aerosol flow out of the container. Already at pressures of 10 mbar, the control means automatically controls the flow rate within the flow channel and automatically controls the tidal flow.

The low pressure generated during the aerosol inhalation directly reduces the cross-section of the flow channel on account of the flexible wall, i.e. directly to a threshold value. Thus, the tidal flow threshold value is already reached at the beginning of the inhalation and essentially kept during the entire inhalation at pressures of 80 to 100 mbar, which are usually generated by the suction of the lungs.

The means for disbursing an aerosol from an aerosol dispenser into the container prevents a drug, such as corticoids, in the form of an aerosol from being dispensed directly from the aerosol dispenser into the oral cavity and from being inhaled. Rather, the patient is required to introduce the aerosol from the aerosol dispenser into the container and subsequently inhale the predetermined aerosol volume defined by the container by means of the inhalation according to the present invention. Preferably, the aerosol dispenser, such as a cartridge, is connected with a nozzle via a collar and secured to the inhalation device. The aerosol is introduced into the inside of the container via the nozzle.

The inhalation device according to the invention has a plurality of advantages. The inhalation device according to the invention allows for a uniform and precise drug dosage irrespective of the patient's coordination. On account of the different container volumes, the desired deposition location in the lungs and the desired aerosol amount is pre-selectable. If the housing is at least in part transparent, the inhaled volume may be controlled visually since the patient is capable of observing the container folding up. The inhalation device according to the invention allows for a simple handling and at the same time a high effectiveness. By dispensing the active ingredient into the container before the inhalation, the aerosol disbursement from the dispenser is restricted to the necessary amount so as to prevent excessive consumption. An accurate and efficient dosage results in low treatment costs, e.g., for a treatment with corticoids. A further advantage of the present invention consists in that the use of a propellant, e.g., for the administration of corticoids, is not absolutely necessary.

The term "suitable drugs" as used here includes active ingredients, drugs, compounds, compositions or mixtures of substances that have a pharmacological, often advantageous effect. Food, dietary supplements, nutrients, drugs, vaccines, vitamins and other useful active ingredients are thus included. The terms used here furthermore include all physiologically or pharmacologically active ingredients having a local or systemic effect in a patient. The active ingredient that may by administered in aerosol form includes antibodies, antiviral substances, anti-epileptics, analgesics, anti-inflammatory substances and bronchodilators and can be an organic or inorganic composition which, without any restrictions, includes drugs having an effect on the peripheral nervous system, adrenergic receptors, cholinergic receptors, skeletal muscles, cardiovascular system, unstriated muscles, circulatory system, neuronal junctions, endocrine or hormonic system, immune system, reproductive system, skeletal system, food intake and excretory system, histamine cascade or central nervous system. Suitable active ingredients may, e.g., be polysaccharides, steroids, hypnotics and sedatives, stimulants, tranquilizers, anticonvulsives and muscular relaxants, anti-parkinson drugs, analgesics, anti-inflammatory agents, antimicrobial substances, antimalarial drugs, hormones including contraceptives, symphaticomimetics, polypeptides and proteins having physiologic effects, diuretics, substances regulating the lipometabolism, anti-androgenic substances, antiparasitics, neoplastics and antineoplastics, antidiabetics, foodstuff and dietary supplements, growth-stimulating substances, fats, bowel regulators, electrolytes, vaccines and diagnostic agents. Combinations of active ingredients (compound preparations) are also possible. Moreover, systemic drugs (such as insulin) may also be administered.

The present invention is particularly suited for (but not restricted to) the application of different active ingredients by inhalation, such as:

Insulin, calcitonin, erythropoietin (EPO), Factor VIII, Factor IX, cyclosporin, granulocyte colony stimulating factor (GCSF), alpha-1 proteinase inhibitor, elcatonin, granulocyte makrophage colony stimulating factor (GMCSF), growth hormones, human growth hormones (HGH), growth hormone releasing hormones (GHRH), heparin, low-molecular weight heparin (LMWH), interferon alpha, interferon beta, interferon gamma, interleukin-2, luteinizing hormone releasing hormone (LHRH), somatostatin, somatostatin analogues including octreotide, vasopressin analogues, follicle stimulating hormone (FSH), insulin-like growth factor, insulinotropin, interleukin-1 receptor antagonist, interleukin-3, interleukin-4, interleukin-6, macrophage colony stimulating factor (MCSF), nerve growth factor, parathyroid hormone (PTH), thymosin alpha 1, IIb/IIIa inhibitor, alpha-1 antitrypsin, antibodies against respiratory syncytical viruses, cystic fibrosis transmembrane regulator gene (CFTR), desoxyribonuclease (DNase), bactericides, permeability-increasing protein (BPI), anti-CMV antibodies, interleukin-1 receptor, retinol, retinyl ester, tocopheroles and their esters, tocotrienols and their esters, carotinoides, in particular beta carotene and other natural and synthetic anti-oxidants, retinol acids, pentamidines, albuterol sulfate, metaproterenol sulfate, beclomethasone diprepionate, triamcinolone acetamide, budesonide acetonide, ipratropium bromide flunisolides, fluticasones, cromolyn sodium, ergotamine tartrate and their analogues, agonists and antagonists of the aforementioned substances. Active ingredients may further include nucleic acids in the form of pure nucleic acid molecules, viral vectors, associated viral particles, nucleic acids associated with or contained in lipids or a lipid-containing material, plasmid DNA or RNA or other nucleic acid constructs suitable for cell transfection or transformation, particularly in cells of the alveolic parts of the lungs. The active ingredient may have different forms, such as soluble or insoluble loaded or unloaded molecules, components of molecular complexes or pharmacologically accepted adjuvants. The active ingredient may consist of natural molecules or their recombinantly produced molecules, or the molecules may be analogues of the natural or recombinantly produced active ingredients in which one or more amino acids have been added or deleted. Moreover, the active ingredient may comprise weakened virus vaccines or dead viruses for vaccination. In case of the active ingredient insulin, naturally extracted human insulin, recombinant human insulin, bovine and porcine extracted insulin, recombinant porcine and bovine insulin and mixtures of the aforementioned insulin types. The insulin may be pure, i.e. substantially purified, but can also comprise commercially available extracts. The term "insulin" also comprises insulin analogues in which one or more of the amino acids of the natural or recombinant insulin have been added or deleted. In particular, the inhalation device according of the present invention is suitable for the administration of vitamin A or vitamin A ester and retinoic acid or retinoic acid ester, also in combination with natural and synthetic antioxidants.

BRIEF DESCRIPTION OF THE DRAWINGS

In the following, the invention will be illustrated with reference to the attached drawings, in which:

FIG. 3a shows a cross-sectional view of a housing of the controllable valve shown in FIGS. 1 and 2;

FIG. 3b shows a lateral view of the housing according to FIG. 3a from the right side;

FIG. 3c shows a lateral view of the housing according to FIG. 3a from the lift side;

FIG. 4a shows a front view of a first component of a set piston for use in the controllable valve according to FIGS. 1 and 2;

FIG. 4b shows a lateral view of the set piston component according to FIG. 4a from the right side;

FIG. 4c shows a lateral view of the set piston component according to FIG. 4a from the lift side;

FIG. 4d shows a cross-sectional view of a set piston component according to FIG. 4a;

FIG. 4e shows a front view of a second set piston component;

FIG. 4f shows a lateral view of the second set piston component according to FIG. 4e from the right side;

FIG. 4g shows a lateral view of the second set piston component according to FIG. 4e from the left side;

FIG. 4h shows a cross-sectional view along the line IVh-IVh of FIG. 4g;

FIG. 4i shows a cross-sectional view along the line IVi-IVi of FIG. 4f;

FIG. 4k shows a front view of a set piston consisting of the first and second set piston components;

FIG. 4*l* shows a cross-sectional view of the assembled set piston according to FIG. 4*k*;

FIG. 5*a* shows a front view of an adjusting screw used in a controllable valve according to FIGS. 1 and 2;

FIG. 5*b* shows a cross-sectional view of an adjusting screw according to FIG. 5*a*;

FIG. 5*c* shows a lateral view of the adjusting screw according to FIG. 5*a* from the left side;

FIG. 6*a* shows a lateral view of a membrane or elastomer disk for use in the controllable valve according to FIGS. 1 and 2;

FIG. 6*b* shows a cross-sectional view of the membrane or elastomer disk according to FIG. 6*a*;

FIG. 7*a* shows a lateral view of a pressure plate for use in the controllable valve according to FIGS. 1 and 2;

FIG. 7*b* shows a front view of the pressure plate according to FIG. 7*a*;

FIG. 8*a* shows a lateral view of a locking screw usable in the controllable valve according to FIGS. 1 and 2;

FIG. 8*b* shows a front view of the locking screw according to FIG. 8*a*;

FIG. 9*a* shows a front view of the housing with a controlling unit according to FIGS. 1 and 2;

FIG. 9*b* shows a lateral view of the hosing with controlling unit according to FIG. 9*a* from the left side;

FIG. 10 shows a cross-sectional view of a second embodiment of a controllable valve which is gradually adjustable;

FIG. 13*a* shows a cross-sectional view of the adjusting screw for the controllable valve according to FIGS. 10 and 11;

FIG. 13*b* shows a cross-sectional view along the line XIIIb-XIIIb of FIG. 13*a*; and FIG. 13*c* shows a lateral view of the adjusting screw according to FIG. 13*a* from the left side.

DETAILED DESCRIPTION

Figure 1:
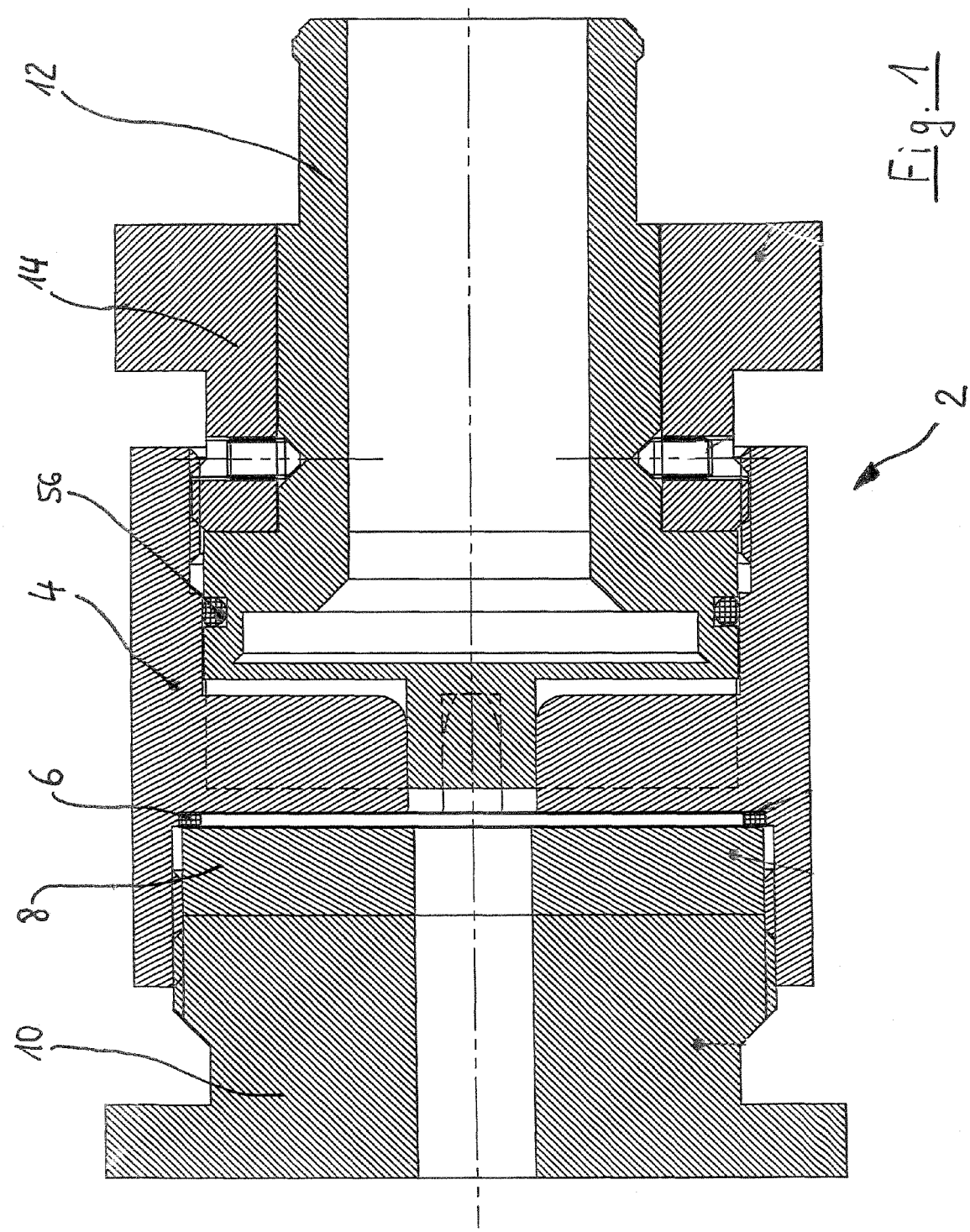
FIG. 1 shows a cross-sectional view of a first embodiment of the invention of an assembled controllable valve according to the invention for use in an inhalation device.
Figure 2:
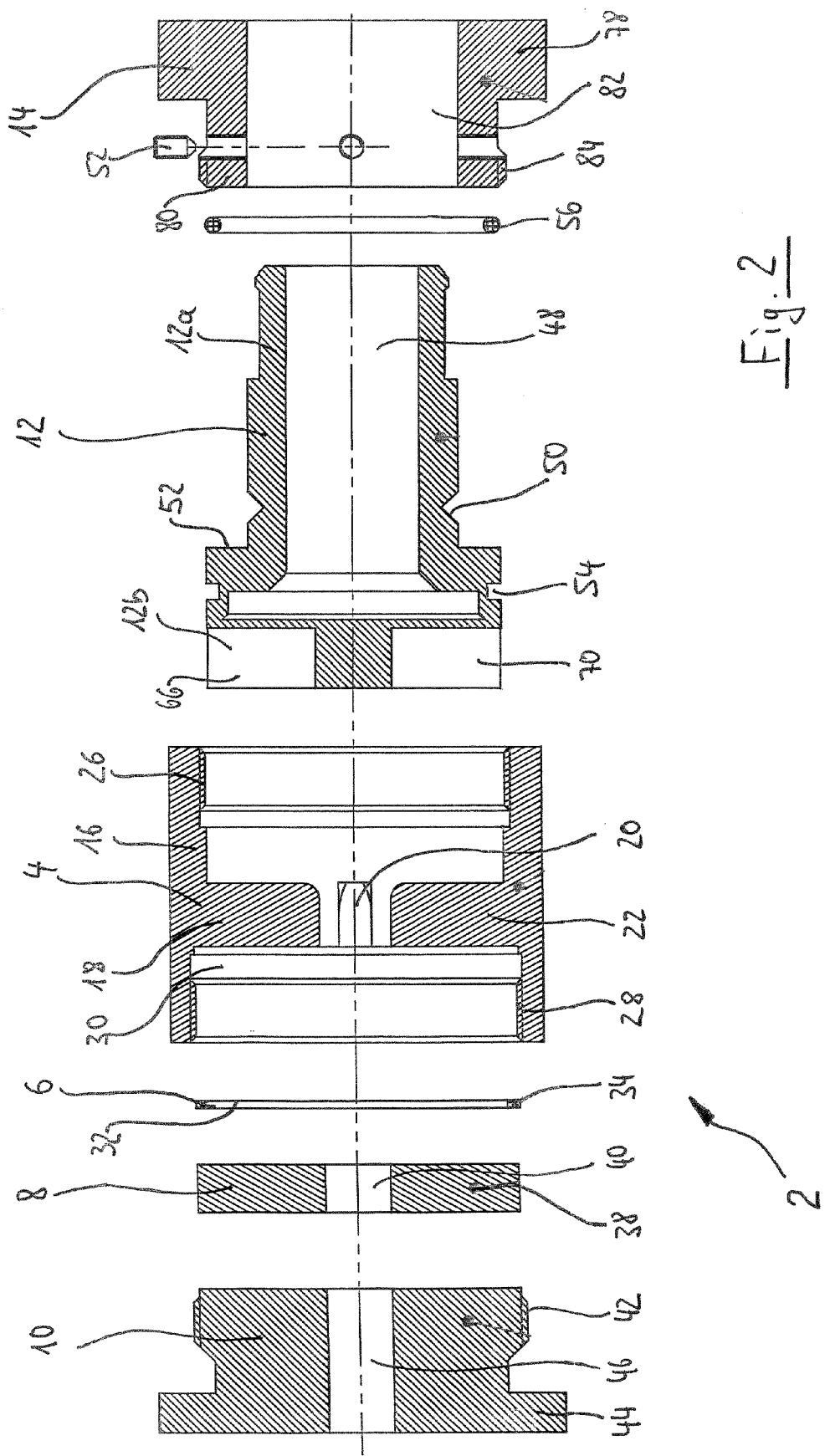
FIG. 2 shows an exploded, cross-sectional view of the controllable valve according to FIG. 1.
Figure 11:
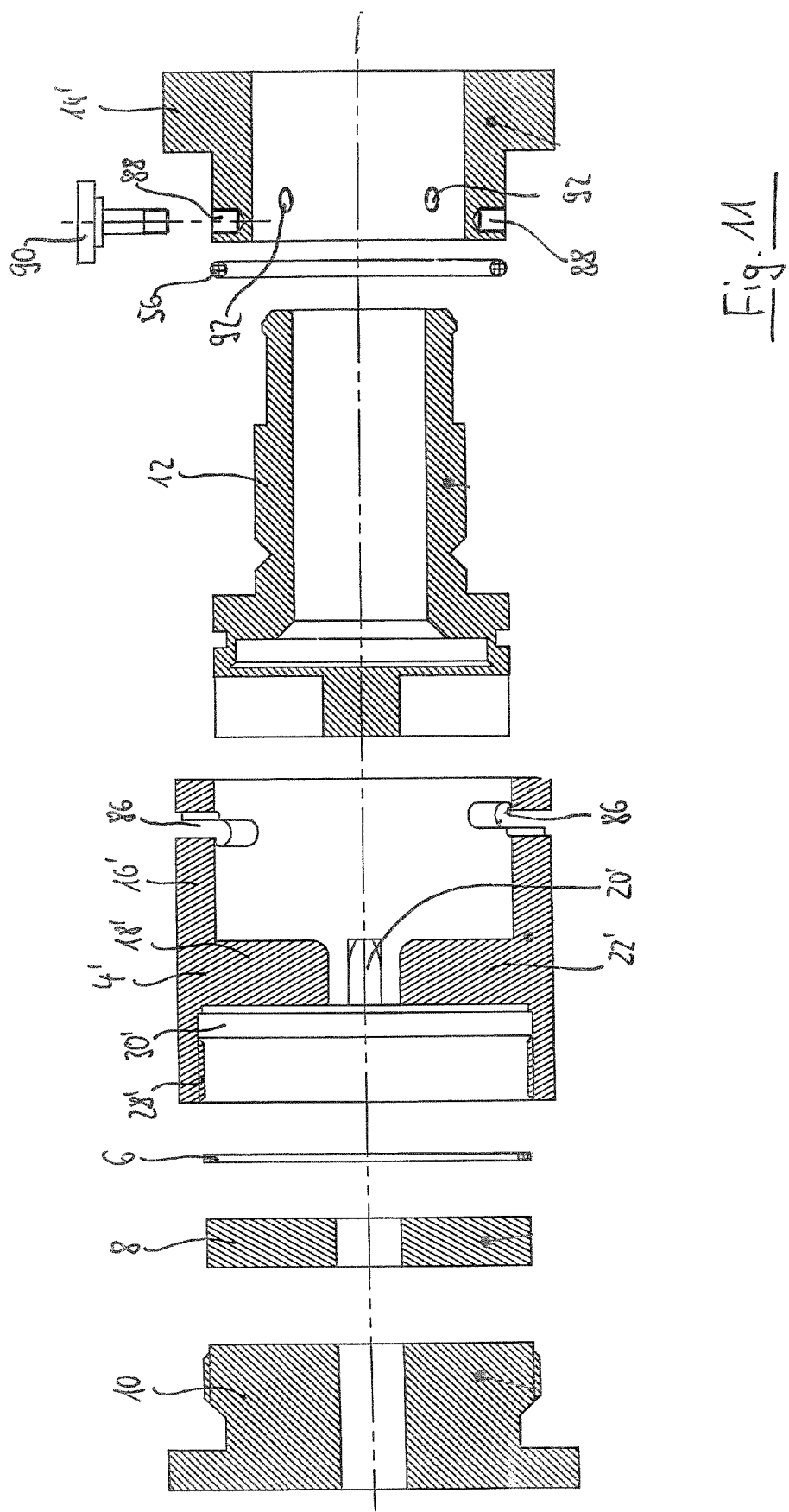
FIG. 11 shows an exploded, cross-sectional view of a controllable valve according to FIG. 10.

The controllable valve 2 according to the invention will be described in the following in combination with an inhalation device comprising in particular a container (not shown) for a predetermined aerosol volume, means (not shown) for introducing or disbursing an aerosol from an aerosol dispenser into the container and control means keeping the inhalation flow essentially constant during the entire aerosol inhalation. The control means essentially consists of the controllable valve 2.

Alternatively, the inhalation device is provided with a spacer or is, e.g., an MDI (metered dose inhaler) or DPI (dry powder inhaler) or nebulizer (ultrasound or compressed air). The term "inhalation device" moreover includes training or diagnostic devices.

According to the embodiment shown in FIGS. 1-9, the controllable valve 2 according to the invention is a continuously adjustable flow limiter.

The controllable valve 2 essentially comprises a housing 4, a membrane or elastomer disk 6, a pressure plate 8, a closure element 10, an axially movable set piston 12 and an adjusting screw 14 for adjusting the flow rate through the controllable valve 2.

The housing 4 of the controllable valve 2 is shown in detail in FIGS. 3*a*, 3*b* and 3*c*. As evident in particular from FIG. 3*a*, the housing 4 having a tubular wall 16 is essentially cylindrical. The housing 4 is provided with a plurality of, preferably four, radially arranged webs 18, 20, 22, 24, wherein one web 24 is longer than the other webs. In the embodiment of the housing 4 shown in FIGS. 3*a*, 3*b* and 3*c*, the webs 18, 20, 22, 24 are inserted into and glued to the tubular wall 16 of the housing 4. Alternatively, the housing could also be formed of one piece.

In the axial direction on one side of the webs 18, 20, 22, 24, the housing 4 is provided with an internal thread 26 for adjustably receiving the set piston 12 via the adjusting screw 14. On the axially opposite side of the webs 18, 20, 22, 24, the housing 4 is also provided with an internal thread 28 for receiving the closure element 10, which is preferably a locking screw. Moreover, on the side of the thread 28, a groove 30 for receiving the membrane or elastomer disk 6 is provided.

The membrane or elastomer disk 6 is shown in detail in FIGS. 6*a* and 6*b* and is preferably disk-shaped having an inner disk portion 32 as well as a collar 34. The centre of the membrane 6 is provided with an opening 36.

The pressure plate 8 is illustrated in FIGS. 7*a* and 7*b*. The pressure plate is essentially a cylindrical plate 38 having a central opening 40 and is provided to hold the membrane 6 in the housing 4 in the groove 30 without any danger of damage to the membrane 6 during the assembly or operation.

The membrane 6 as well as the pressure plate 8 are preferably fixed by the locking screw 10, which may be screwed into the housing 4 using an external thread 42 that engages with the thread 28 at the housing 4. The locking screw 10 is moreover provided with a knob 44 for operating the locking screw 10. Moreover, the locking screw 10 is provided with a central through hole 46 that is essentially aligned with the through hole 40, the pressure plate 8 as well as the through hole 36 of the membrane 6.

If assembled, the membrane 6 is forced into a predetermined and set position by means of the pressure plate 8 and the locking screw 10. In this position, the inner disk portion 32 of the membrane rests on the webs 18, 20, 22, 24 of the housing 4. The collar 34 of the membrane 6 extends away from the webs 18, 20, 22, 24. This is clearly shown in FIG. 1.

The set piston 12 of the controllable valve 2 is illustrated in FIGS. 4*a*-4*l* in detail. According to FIGS. 4*a*-4*d*, the set piston 12 is provided with a first set piston component 12*a* and, according to FIGS. 4*e*-4*i*, with a second set piston component 12*b*. A front view of the first set piston component 12*a* is shown in FIG. 4*a* and lateral views thereof from the right and left sides are shown in FIGS. 4*b* and 4*c*, respectively. FIG. 4*d* shows a cross-sectional view through the first set piston component 12*a*.

Figure 12C:
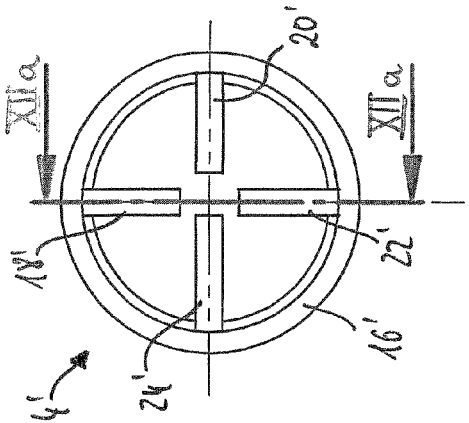
FIG. 12*c* shows a lateral view of the housing according to FIG. 12*a* from the left side.
Figure 12A:
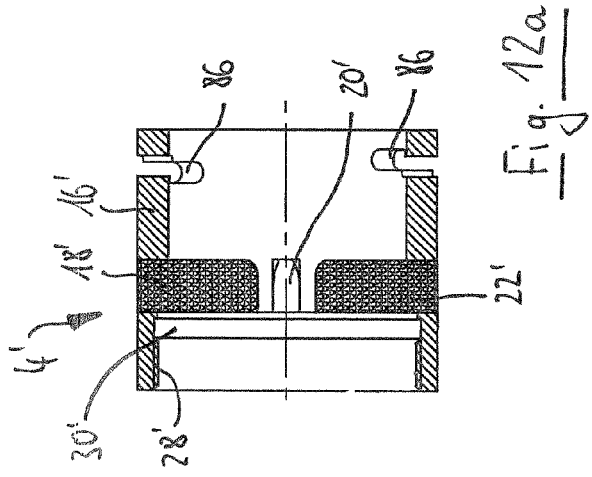
FIG. 12*a* shows a cross-sectional view of the housing of a controllable valve according to FIGS. 10 and 11.
Figure 12B:
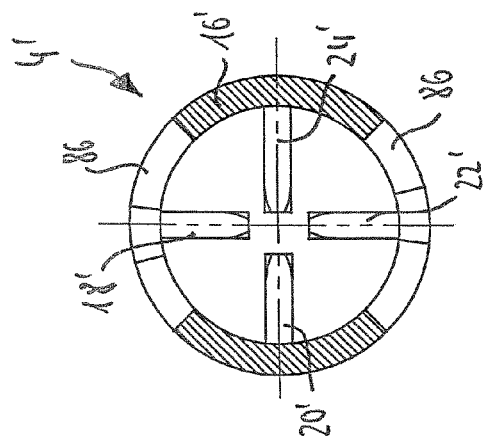
FIG. 12*b* shows a cross-sectional view of the housing according to FIG. 12*a* along the line XIIb-XIIb.
Figure 12D:
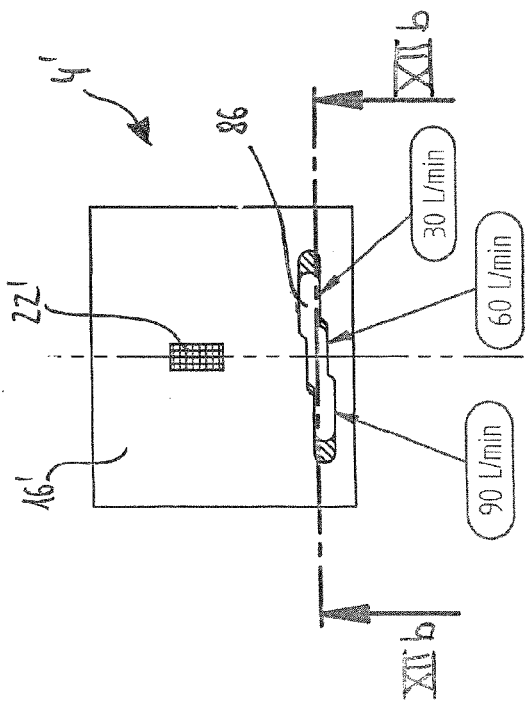
FIG. 12*d* shows a front view of the housing according to FIG. 12*a*.

The first set piston component 12*a* is provided with a through hole or a central flow channel 48, which is in particular well recognisable in FIG. 12*d*. Moreover, the first set piston component 12*a* is provided with a circumferential groove 50 for receiving one or more setting screws 52, such as grub screws, with which the adjusting screw 14 is axially fixed to the set piston 12. Moreover, the first set piston component 12*a* is provided with a limit stop 52 for the adjusting screw 14. Moreover, the first set piston component 12*a* comprises a circumferential groove 54 for receiving a sealing ring 56 as well as a protrusion 58 and a limit stop 60 for receiving the second set piston component 12*b*.

As in particular shown in FIG. 4*h*, the second piston component 12*b* is provided with a recess 62 for receiving the protrusion 58 as well as a collar 64 that may be contacted with the limit stop 60. In this area, the first and second set piston components 12a, 12b are preferably glued together so as to form a one-part component.

As shown in FIG. 4e, the second set piston component 12b consists of an essentially cylindrical element which, according to the lateral view shown in FIG. 4g, comprises four recesses 66, 68, 70, 72 that are formed so as to match the webs 18, 20, 22, 24 in the housing 4. Thus, one recess 72 is longer than the other recesses 66, 68, 70. When the set piston 12 is inserted into the housing 4, the recesses 66, 68, 70, 72 receive the webs 18, 20, 22, 24 in correspondence with the respective axial position of the set piston 12 with respect to the housing 4. This is clearly shown in FIG. 1.

In the area between two adjoining recesses, the second set piston component 12b is provided with several openings 74, as shown in FIGS. 4f and 4g. These openings 74 run into a flat channel 76, which is shown in detail in FIGS. 4h and 4i and fluidically connects pairs of adjoining openings 74 between two webs. The flow channels 76 of the second set piston component 12b, however, run into the flow channel 48 of the first set piston component 12a.

The adjusting screw 14 is shown in detail in FIGS. 5a, 5b and 5c. The adjusting screw 14 has a handle portion 78, an engagement portion 80 as well as a central through hole 82. The engagement portion 80 is provided with an external thread 84 that is engageable with the thread 26 of the housing 4 so as to position the set piston 12 axially in the housing. The adjusting screw 14 and the set piston 12 are connected by the grub screw(s) 52 that engage(s) with the groove 50 at the set piston so as to prevent the two components from axially shifting relative to each other. To this end, the circumference of the adjusting screw is provided with a plurality of grub screws 52, preferably four grub screws that are displaced from each other by 90°.

FIGS. 9a and 9b again show the housing 4 and the adjusting mechanisms 12, 14 in assembled (uncut) form. In particular the lateral view from the left side of FIG. 9b, in which the locking screw 10 and the pressure plate 8 are not shown, clearly illustrates that the wall 16 of the housing 4 limits the controllable valve radially outwards, while the four webs 18, 20, 22, 24 extend essentially radially inwards. The second set piston component 12b, and in particular the openings 74 thereof is/are also identifiable in the view according to FIG. 9b. The membrane 6 is depicted transparent in FIG. 9b and rests on the webs 18, 20, 22, 24 as well as in the groove 30. The collar 34 of the membrane is represented by the dashed lines in FIG. 9b just like the central opening 36 of the membrane 6.

The first embodiment of the controllable valve 2 according to the present invention described above with reference to FIGS. 1-9 allows for a continuously, variably adjustable flow rate through the valve.

FIGS. 10-13 show a second embodiment of a controllable valve 2' according to the present invention, in which the flow rate through the valve is gradually adjustable, e.g., in three steps. FIG. 10 shows a cross-sectional view of an assembled controllable valve 2'. The valve 2' comprises a housing 4', a membrane or elastomer disk 6, a pressure plate 8, a locking screw 10, a set piston 12 as well as an adjusting screw 14'. Unless explicitly mentioned, the elements of the controllable valve 2' of the second embodiment correspond to those of the first embodiment.

The housing 4' of the controllable valve according to the second embodiment is shown in FIGS. 12a, 12b, 12c and 12d in more detail. The housing 4' is also essentially tubular and comprises a wall 16' as well as four webs 18', 20', 22', 24'. Moreover, a thread 28' is provided for receiving the locking screw 10 as well as a groove 30' for receiving the membrane or elastomer disk 6.

On the side of the webs opposite the groove 30' for receiving the membrane, however, the housing 4' is not provided with a thread for receiving an adjusting screw unlike the first embodiment. Rather, the housing 4' comprises a sliding block guide in the form of one or more axially stepped recesses 86, which is in particular shown in FIG. 12d in more detail. On account of the stepped design of the recess 86, the set piston 12 is adjustable in three different axial positions, e.g. for a volumetric flow rate of 30 l/min, 60 l/min or 90 l/min, as schematically shown in FIG. 12d.

The set piston 12 essentially corresponds to the set piston described in connection with the first embodiment and is axially movably and sealingly guided in the housing 4'.

FIGS. 13a, 13b and 13c show the adjusting screw 14' for the controllable valve 2' of the second embodiment in more detail. As with the first embodiment, the adjusting screw 14' comprises an operating portion 78' as well as an engagement portion 80' and a central flow channel 82'. The adjusting screw 14', however, is not provided with an external thread for being connected to the housing but rather comprises radially arranged threaded pocket holes 88 into which sliding block screws 90 may be screwed through the recess(es) 86 in the housing 4'. Moreover, as in the first embodiment, the adjusting screw 14' is provided with the tap holes 92 that are provided to receive the grub screws 52 so as to axially fixate the adjusting screw 14' with respect to the set piston 12.

According to the present invention, various embodiments of the controllable valve and inhalation device comprising these components are possible. Some of these alternative embodiments are listed below. Reference numerals for the features of the controllable valve device components described above are included in the various listed embodiments.

1. An inhalation device comprising a control means that keeps the inhalation flow essentially constant during the entire aerosol inhalation, characterised in that the control means comprises a controllable valve (2; 2').

2. The inhalation device according to embodiment 1, further comprising a container for a predetermined aerosol volume, means for disbursing an aerosol from an aerosol dispenser into the container as well as an aerosol dosing supply, a nebulizer and/or an inhalation aid.

3. The inhalation device according to embodiments 1 or 2, wherein the controllable valve is a continuously variable flow limiter (2).

4. The inhalation device according to embodiments 1 or 2, wherein the controllable valve is a flow limiter (2) that is adjustable in several steps.

5. The inhalation device according to any of embodiments 1 to 4, wherein the controllable valve (2; 2') comprises a housing (4; 4'), a membrane (6), an optional pressure plate (8), a closure element (10), a set piston (12) and an adjusting screw (14; 14').

6. The inhalation device according to embodiment 5, wherein the housing (4; 4') is essentially tubular and comprises a plurality of, preferably four, radially arranged webs (18, 20, 22, 24; 18', 20', 22', 24'), one web (24; 24') being longer than the others.

7. The inhalation device according to embodiment 6, wherein on the one side of the webs the housing (4; 4') is designed so as to adjustably receive the set piston (12) and on the opposite side so as to receive the membrane (6), the pressure plate (8) and the closure element (10).

8. The inhalation device according to any of embodiments 5 to 7, wherein the membrane (6) is forced against the webs (18, 20, 22, 24; 18', 20', 22', 24') of the housing (4; 4') by the pressure plate (8) and the closure element (10) so that a space is formed between the membrane (6) and the set piston (12).

9. The inhalation device according to any of embodiments 5 to 8, wherein the membrane (6) is disk-shaped and provided with a collar (34) at its edge.

10. The inhalation device according to any of embodiments 6 to 9, wherein the set piston (12) comprises a plurality of, preferably four, radially arranged recesses (66, 68, 70, 72) corresponding to the webs (18, 20, 22, 24; 18', 20', 22', 24') of the housing (4; 4') at its front end facing the membrane (6), one recess (72) being longer than the others.

11. The inhalation device according to any of embodiments 5 to 10, wherein the set piston (12) is sealingly received in the housing (4; 4').

12. The inhalation device according to any of embodiments 5 to 11, wherein the adjusting screw (14; 14') is axially fixable to the set piston (12) and the set piston (12) is axially adjustable with respect to the housing (4; 4') via the adjusting screw (14; 14').

13. The inhalation device according to any of embodiments 6 to 12, wherein the adjusting screw (14; 14') comprises one, preferably two, opening(s) (74) in the area between two adjoining recesses.

14. The inhalation device according to embodiment 13, wherein between each pair of adjoining recesses (66, 68, 70, 72) two openings (74) are provided which are situated on a common circumferential line and are spaced apart from each other by approx. 45°.

15. The inhalation device according to any of embodiments 6 to 14, wherein at least portions of the housing (4; 4'), the membrane (6), the pressure plate (8), the closure element (10) and the set piston (12) are provided with a central flow channel.

16. The inhalation device according to any of embodiments 4 to 15, wherein the adjusting screw (14) is screwed into the housing (4).

17. The inhalation device according to any of embodiments 4 to 15, wherein the adjusting screw (14') is connected to the housing (4') via a sliding block guide (86, 90) so as to axially guide the set piston (12).

18. A controllable valve, in particular for use in an inhalation device, comprising:
a housing (4; 4'), a membrane (6), an optional pressure plate (8), a closure element (10), a set piston (12) and an adjusting screw (14; 14'), wherein the housing (4; 4') is essentially tubular and comprises a plurality of, preferably four, radially arranged webs (18, 20, 22, 24; 18', 20', 22', 24'), one web (24; 24') being longer than the others, wherein on one side of the webs the housing (4; 4') is designed so as to adjustably receive the set piston (12) and on the opposite side so as to receive the membrane (6), the optional pressure plate (8) and the closure element (10).

19. The controllable valve according to embodiment 18, wherein the membrane (6) is forced against the webs (18, 20, 22, 24; 18', 20', 22', 24') of the housing (4; 4') by means of the pressure plate (8) of the closure element (10) so that a space is formed between the membrane (6) and the set piston (12).

20. The controllable valve according to embodiments 18 or 19, wherein the membrane (6) is disk-shaped and is provided with a collar (34) at its edge.

21. The controllable valve according to any of embodiments 18 to 20, wherein at its front end facing the membrane (6) the set piston (12) comprises a plurality of, preferably four, radially arranged recesses (66, 68, 70, 72) corresponding to the webs (18, 20, 22, 24; 18', 20', 22', 24') of the housing (4; 4'), one recess (72) being longer than the others.

22. The controllable valve according to any of embodiments 18 to 21, wherein the set piston (12) is sealingly received within the housing (4; 4').

23. The controllable valve according to any of embodiments 18 to 22, wherein the adjusting screw (14; 14') is axially fixable to the set piston (12) and the set piston (12) is axially adjustable with respect to the housing (4; 4') by means of the adjusting screw 14; 14').

24. The controllable valve according to any of embodiments 18 to 23, wherein in the area between two adjoining recesses the adjusting screw (14, 14') is provided with at least one, preferably two opening(s) (74).

25. The controllable valve according to embodiment 24, wherein each pair of adjoining recesses (66, 68, 70, 72) is provided with two openings (74) which are situated on a common circumferential line and are spaced apart from each other by approx. 45°.

26. The controllable valve according to any of embodiments 18 to 25, wherein at least portions of the housing (4; 4'), the membrane (6), the pressure plate (8), the closure (10) and the set piston (12) are provided with a central flow channel.

27. A controllable valve according to any of embodiments 18 to 26, wherein the adjusting screw (14) is screwed into the housing (4).

28. The controllable valve according to any of embodiments 18 to 26, wherein the adjusting screw (14') is connected to the housing (4') by means of a sliding block guide (86, 90) so as to axially guide the set piston (12).

29. The controllable valve according to any of embodiments 18 to 28 in the form of a continuously variable flow limiter.

30. The controllable valve according to any of embodiments 18 to 28 in the form of a flow limiter that is adjustable in several steps.

31. The controllable valve according to any of embodiments 18 to 30, wherein the valve is connected to an inhalation flow rate limitation.

32. The controllable valve according to embodiment 31, wherein the flow rate limitation is directly or indirectly performed over time.

The invention is further set forth in the claims listed below. This invention may take on various modifications and alterations without departing from the spirit and scope thereof. In describing embodiments of the invention, specific terminology is used for the sake of clarity. The invention, however, is not intended to be limited to the specific terms so selected, and it is to be understood that each term so selected includes all technical equivalents that operate similarly.

The invention claimed is:

1. An inhalation device comprising a control means having a flow channel therethrough, the control means keeping the inhalation flow essentially constant during an entire aerosol inhalation by reducing a cross-section of the flow channel, wherein the control means comprises a controllable valve including a housing, a closure element, a membrane forming a wall of the flow channel, the membrane arching into the flow channel, thereby reducing the cross-section of the flow channel, in response to a lowered pressure within the housing, a pressure plate, a set piston and an adjusting screw secured to the set piston and axially adjustable relative to the housing in order to adjust the flow rate through the controllable valve.

2. The inhalation device according to claim 1, wherein the controllable valve is a continuously variable flow limiter.

3. The inhalation device according to claim 1, wherein the controllable valve is a flow limiter that is adjustable in several steps.

4. The inhalation device according to claim 1, wherein the housing is essentially tubular and comprises a plurality of radially arranged webs, one web being longer than the others.

5. The inhalation device according to claim 4, wherein on the one side of the webs the housing is designed so as to adjustably receive the set piston and on the opposite side so as to receive the membrane, the pressure plate and the closure element.

6. The inhalation device according to claim 4, wherein the membrane is forced against the webs of the housing by the pressure plate and the closure element so that a space is formed between the membrane and the set piston.

7. The inhalation device according to claim 1, wherein the membrane is disk-shaped and provided with a collar at its edge.

8. The inhalation device according to claim 4, wherein the set piston comprises a plurality of radially arranged recesses corresponding to the webs of the housing at its front end facing the membrane, one recess being longer than the others.

9. The inhalation device according to claim 1, wherein the set piston is sealingly received in the housing.

10. The inhalation device according to claim 1, wherein the adjusting screw is axially fixable to the set piston and the set piston is axially adjustable with respect to the housing via the adjusting screw.

11. The inhalation device according to claim 8, wherein the adjusting screw comprises at least one opening in an area between two adjoining recesses of the plurality of radially arranged recesses.

12. The inhalation device according to claim 11 further comprising at least one pair of adjoining recesses and between each pair of which two openings are provided which are situated on a common circumferential line and are spaced apart from each other by approx. 45°.

13. The inhalation device according to claim 4, wherein at least portions of the housing, the membrane, the pressure plate, the closure element and the set piston are provided with a central flow channel.

14. The inhalation device according to claim 1, wherein the adjusting screw is screwed into the housing.

15. The inhalation device according to claim 1, wherein the adjusting screw is connected to the housing via a sliding block guide so as to axially guide the set piston.

16. A controllable valve having a flow channel therethrough for use in an inhalation device, comprising:

a housing, a membrane, a pressure plate, a closure element, a set piston and an adjusting screw for adjusting a flow rate through the controllable valve, wherein the housing is essentially tubular and comprises a plurality of radially arranged webs, one web being longer than the others, wherein on one side of the webs the housing is designed so as to adjustably receive the set piston in order to adjust the flow rate through the controllable valve and on the opposite side so as to receive the membrane, the optional pressure plate and the closure element, and wherein the membrane forms part of the flow channel and arches into the flow channel in response to a lowered pressure within the housing.

17. The controllable valve according to claim 16, wherein the membrane is forced against the webs of the housing by means of the pressure plate of the closure element so that a space is formed between the membrane and the set piston.

18. The controllable valve according to claim 16, wherein the membrane is disk-shaped and is provided with a collar at its edge.

19. The controllable valve according to claim 16, wherein at its front end facing the membrane the set piston comprises a plurality of radially arranged recesses corresponding to the webs of the housing, one recess being longer than the others.

20. The controllable valve according to claim 16, wherein the set piston is sealingly received within the housing.

21. The controllable valve according to claim 16, wherein the adjusting screw is axially fixable to the set piston and the set piston is axially adjustable with respect to the housing by means of the adjusting screw.

22. The controllable valve according to claim 16, wherein in an area between adjoining recesses the adjusting screw is provided with at least one opening.

23. The controllable valve according to claim 22, wherein each pair of adjoining recesses is provided with two openings which are situated on a common circumferential line and are spaced apart from each other by approx. 45°.

24. The controllable valve according to claim 16, wherein at least portions of the housing, the membrane, the pressure plate, the closure and the set piston are provided with a central flow channel.

25. A controllable valve according to claim 16, wherein the adjusting screw is screwed into the housing.

26. The controllable valve according to claim 16, wherein the adjusting screw is connected to the housing by means of a sliding block guide so as to axially guide the set piston.

27. The controllable valve according to claim 16 in the form of a continuously variable flow limiter.

28. The controllable valve according to claim 16 in the form of a flow limiter that is adjustable in several steps.

29. The controllable valve according to claim 16, wherein the valve is used in an inhalation device to keep the inhalation flow rate essentially constant during an entire aerosol inhalation cycle.

* * * * *